United States Patent [19]
Monte et al.

[11] Patent Number: 5,874,601
[45] Date of Patent: Feb. 23, 1999

[54] PROCESS OF PROTECTING A 1,2-AMINOALCOHOL FOR REDUCTIVE AMINATION COUPLING

[75] Inventors: William T. Monte, Grayslake; Aline C. Lindbeck, Waukegan, both of Ill.

[73] Assignee: Abbott Laboratories, Abbott Park, Ill.

[21] Appl. No.: 628,367

[22] Filed: Apr. 5, 1996

[51] Int. Cl.$^6$ ....................................................... C07F 7/10
[52] U.S. Cl. ......................... 556/413; 556/410; 560/190; 560/196; 564/374; 564/382
[58] Field of Search ..................... 556/413, 410; 560/190, 196; 564/374, 382

[56] References Cited

U.S. PATENT DOCUMENTS

| | | |
|---|---|---|
| 5,130,468 | 7/1992 | Kempf . |
| 5,486,633 | 1/1996 | Pirrung et al. ....................... 556/413 X |
| 5,523,442 | 6/1996 | Collard et al. ........................... 556/413 |

FOREIGN PATENT DOCUMENTS 0329464  8/1989  European Pat. Off. .

OTHER PUBLICATIONS

Pierce, *Silylation of Organic Compounds*, Rockford, IL, Jun. 1968, pp. 73–75, 81, and 476.

Iwase, H., et al., "Gas Chromatography–Mass Spectrometry of Trimethylsilyl Derivatives of Amines", *Chem. Pharm. Bull.*, 27(4):1009–1014 (1979).

Greene, T. W., et al., "Protective groups in organic synthesis", *John Wiley & Sons, New York*, 68–73 & 406–414.

*Primary Examiner*—Paul F. Shaver
*Attorney, Agent, or Firm*—Michael J. Ward

[57] ABSTRACT

A process of protecting a 1,2- or 1,3-aminoalcohol for reductive amination coupling is provided. The alcohol is protected with trimethylsilyl chloride. Trimethylsilyl protected norepinephrine derivatives useful in the preparation of arbutamine are also provided.

9 Claims, 1 Drawing Sheet

5,874,601

PROCESS OF PROTECTING A 1,2-AMINOALCOHOL FOR REDUCTIVE AMINATION COUPLING

TECHNICAL FIELD OF THE INVENTION

The field of the present invention is alcohol protection in a reductive amination coupling reaction. More particularly, the present invention pertains to a process of protecting a 1,2- or 1,3-aminoalcohol using trimethylsilyl chloride.

BACKGROUND OF THE INVENTION

The synthesis of many useful compounds involves the coupling of two distinct chemical entities. Where those entities are an amine and an aldehyde, coupling is typically accomplished using reductive amination. For example, the preparation of arbutamine involves the reductive amination coupling of norepinephrine including free base and its salts, with 4-(4-benzyloxyphenyl)butanal to form benzyl arbutamine free base or its salt.

The use of reductive amination coupling to produce a desired product, free of contaminating byproducts, is compromised where the amine is a 1,2- or 1,3-aminoalcohol. The hydroxy group (OH) of the alcohol can react with the aldehyde to form an undesired cyclic amino acetal in addition to the desired hydroxyimine.

In the case of arbutamine preparation, formation of the oxazolidine leads to the synthesis of dialkylated byproducts through reaction of the oxazolidine with a second molecule of aldehyde present in the amination reaction. The presence of the dialkylated byproduct severely interferes with isolation of the desired monoalkylated product and decreases the yield of the desired product.

There continues to be a need for an improved process for the reductive amination of 1,2- or 1,3-aminoalcohols that prevents the formation of unwanted byproducts.

BRIEF SUMMARY OF THE INVENTION

The present invention provides a novel process of protecting 1,2- or 1,3-aminoalcohols to prevent the formation of byproducts when that alcohol is used in a reductive amination coupling reaction. In accordance with that process, the 1,2- or 1,3-aminoalcohol is protected with trimethylsilyl chloride.

The present invention also provides trimethylsilyl-protected aminoalcohols useful as intermediates in the production of compounds via reductive amination couplings. The present invention also provides trimethylsilyl-protected alcohols useful as intermediates in the production of arbutamine.

A process of the present invention is useful in the preparation of pharmaceutical, veterinary, agricultural and other chemical products, the synthesis of which products involve the reductive amination of a 1,2- or 1,3-aminoalcohol. One example of the process of the present invention is the protection of norepinephrine during preparation of arbutamine.

DETAILED DESCRIPTION OF THE INVENTION

Figure 1:
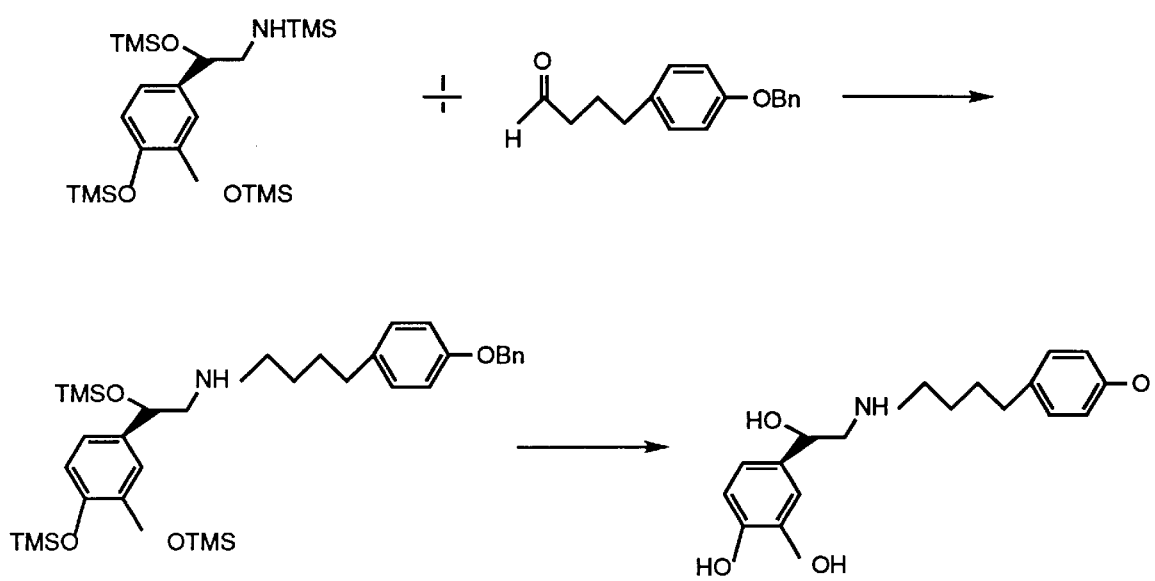
FIG. 1 shows a synthetic scheme for the synthesis of benzyl arbutamine.

A process of the present invention involves protecting 1,2 or 1,3-aminoalcohols, as well as other hydroxy groups associated with the aminoalcohols, with trimethylsilyl chloride before performing reductive amination couplings.

A process of the present invention involves reacting a 1,2- or a 1,3-aminoalcohol with trimethylsilyl chloride. The trimethylsilyl group protects the alcohol (OH) during subsequent reductive amination couplings. Such protection prevents the hydroxy group of the alcohol from reacting with coupling agents and, thus, minimizes the formation of unwanted byproducts.

For example, the reductive amination coupling of a 1,2- or a 1,3-aminoalcohol with an aldehyde can lead to formation of both a hydroxyimine (unreacted hydroxy) as well as an oxazolidine (hydroxy incorporated into a cyclic structure). Oxazolidine formation can be prevented by protecting the hydroxy group(s) before coupling.

Protecting groups were studied for their ability to protect the benzylic hydroxy group of norepinephrine. The most suitable protecting group examined was the trimethylsilyl group. This group was easily put on norepinephrine in situ, and may be used without further purification.

To protect the hydroxy group of the alcohol, the alcohol is reacted with trimethylsilyl chloride in the presence of a suitable base and a suitable solvent. Numerous bases were tested with trimethylsilyl chloride and norepinephrine. Suitable bases used with the process of the present invention include, but are not intended to be limited to, pyridine and triethylamine. Both worked well in trapping the HCl formed during the reaction. However, triethylamine was found to be preferable due to the ease with which its hydrochloride salt could be filtered away after the reaction was complete.

The use of less than four equivalents of trimethylsilyl chloride and trimethylamine gave mixtures of products. Since it was crucial to protect the benzylic hydroxy group on the molecule, it was necessary to fully protect all four nucleophilic sites. The use of at least four equivalents provided the fully protected molecule, as characterized by $^1$H and $^{13}$C-NMR.

Solvents were examined for use in the protection reaction. Solvents which may be used with the process of the present invention include, but are not intended to be limited to, acetonitrile, tetrahydrofuran (THF), methylene chloride, and ethyl acetate.

Preferably, protection of norepinephrine may be accomplished with four equivalents of trimethylsilyl chloride and four equivalents of triethylamine in ethyl acetate. The reaction may be run at or below room temperature for at least eight hours. These conditions yield the fully protected molecule in solution after filtering off the triethylamine hydrochloride. This solution can be used directly in the reductive amination reaction. The near quantitative yield for this reaction was determined indirectly from the weight of the recovered triethylamine hydrochloride.

The trimethylsilyl-protected 1,2- or 1,3-aminoalcohol can then be used in a reductive amination to couple the alcohol with another compound. Reductive amination procedures are well known in the art and will depend inter alia on the structure of the alcohol and the other compound.

Where the protected alcohol is norepinephrine and it is coupled with 4-(4-benzyloxyphenyl)butanal to form benzyl arbutamine free base or its salt, reductive amination is performed as set forth below.

Since one equivalent of water is generated during the coupling reaction, a drying agent is used to prevent the trimethylsilyl-protected norepinephrine from being deprotected and to help drive the equilibrium towards the imine.

Drying agents useful in the process of the present invention include, but are not intended to be limited to, magnesium sulfate and calcium chloride. One preferred drying agent is magnesium sulfate. As the amount of magnesium sulfate is decreased to 2.5 equivalents, the relative ratio of product to dialkylated byproduct begins to drop. This effect becomes dramatic with 1.0 equivalent of magnesium sulfate, where that relative ratio has now dropped to 81/19. Another preferred drying agent is calcium chloride. Calcium chloride required only 2.0 equivalents to as compared to 4.0 equivalents of magnesium sulfate required to achieve the same results. When the reaction was carried out on a larger scale, however, the calcium chloride did not filter as well as the magnesium sulfate.

Following reductive amination coupling, it is necessary to remove the trimethylsilyl protecting groups. In the synthesis of benzyl arbutamine oxalate, the trimethylsilyl-protecting groups are removed and the oxalate salt is formed. Optimal conditions for the removal of the trimethylsilyl protecting groups include the use of a minimal amount of acetic acid (0.1 equivalents) and water, and one full equivalent of oxalic acid. The reaction is done in ethyl acetate at room temperature for 3–5 hours to achieve good yields. The reaction proceeds smoothly using either catalytic water or methanol with comparable isolated yields. Only 0.1 equivalents of acetic acid is required to catalyze the reaction, but without a catalytic amount of acetic acid present, the reaction does not proceed. In general, yields are significantly higher when a full equivalent of oxalic acid is used.

FIG. 1 illustrates a schematic scheme for the synthesis of benzyl arbutamine using the process of the present invention. A detailed description of the synthetic steps can be found in the Examples to follow.

The present invention further provides intermediates useful in the preparation of benzyl arbutamine oxalate. Those intermediates are trimethylsilyl-protected norepinephrine and trimethylsilyl-protected benzyl arbutamine. The structure of trimethylsilyl-protected norepinephrine corresponds to formula I, below:

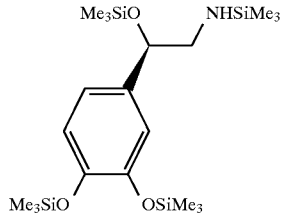

The structure of trimethylsilyl-protected benzyl arbutamine corresponds to formula II, below:

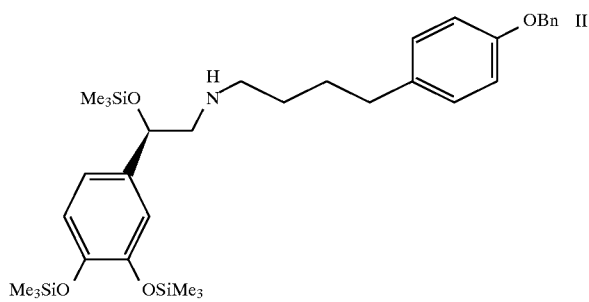

The following Example illustrates a preferred embodiment of the present process and is not limiting of the specification and claims in any way.

EXAMPLE 1

Protection of (R)-Norepinephrine with Trimethylsilyl Chloride

A 3-liter, 3-neck round-bottom flask equipped with mechanical stirrer, 250-mL addition funnel, and condenser was charged with (R)-norepinephrine (33.84 g, 200 mmol) and ethyl acetate (900 mL). The resulting slurry was stirred under nitrogen protection. Triethylamine (80.95 g, 800 mmol) was added dropwise via an addition funnel over a period of approximately 2 minutes. The addition funnel was then rinsed with an additional 40 mL ethyl acetate.

Trimethylsilyl chloride (86.91 g, 800 mmol) was added dropwise via an addition funnel over a period of 30 minutes. The temperature of the reaction mixture rises to 35°–40° C. by the end of the addition. The addition funnel was rinsed with an additional 60 mL ethyl acetate and the mixture was stirred at ambient temperature for 8–18 hours. At this time, the white slurry was vacuum-filtered through Whatman 1 filter paper. The filter cake was washed with an additional 400 mL ethyl acetate and the filtrate used directly in a coupling reaction.

EXAMPLE 2

Preparation of Benzyl Arbutamine Oxalate

A solution of 4-(4-benzyloxyphenyl)-butanal (52.4 g, 206 mmol) in 150 mL ethyl acetate (1.4M solution) was prepared and set aside. 10% platinum on carbon (3.40 g) was prewetted with ethyl acetate and transferred to the reactor. To this was added magnesium sulfate (60.0 g, 500 mmol), followed by the ethyl acetate solution of (trimethylsilyl)-protected norepinephrine prepared as described in Example 1.

The reactor was assembled and evacuated and purged with nitrogen four times. After this sequence, the reactor was evacuated and approximately 25% (35–40 mL) of the aldehyde solution in ethyl acetate was added via an auxiliary valve. After the appropriate amount was added, the teflon line was rinsed with a minimum amount of ethyl acetate. The system was evacuated and purged with nitrogen three to four times, then evacuated and purged with hydrogen three times. Finally, the reactor was pressurized with hydrogen (30–40 psi).

After 20 minutes, the addition step was repeated to add the second portion of aldehyde solution to the reaction mixture. The third and fourth portions were added in a similar fashion at 20-minute intervals. After the last addition of aldehyde solution, the reactor was pressurized with hydrogen and allowed to react until no more hydrogen was consumed (this usually takes between 12 and 18 h after the last aldehyde addition, depending on the scale of the reaction). When this point was reached, the reactor was evacuated and purged with nitrogen four times. The catalyst and magnesium sulfate were removed by vacuum filtration through fiberglass filter paper (ethyl acetate wash). This solution was used directly in the next step.

A 3-liter, 3-neck round-bottom flask equipped with mechanical stirrer, 125 mL addition funnel, and nitrogen inlet was charged with the filtered solution from the coupling reaction. Oxalic acid (18.01 g, 200 mmol) was added as a solid in one portion. The addition funnel was charged with a mixture of acetic acid (1.20 g, 20 mmol) and distilled water (50 mL). With vigorous stirring, the water/acetic acid mixture was added to the reaction mixture quickly over a period of 2 minutes. The reaction was stirred at room temperature and monitored by TLC ($CH_2Cl_2$/MeOH/HOAc:10/2/1).

As the reaction proceeded, a white precipitate came out of solution. When the reaction was complete (usually after 4–16 hours), the milky white mixture was vacuum filtered through Whatman 1 filter paper (ethyl acetate wash). The off-white solid was dried under vacuum at room temperature until constant weight was achieved, giving 83.41 g (84%) of Benzyl Arbutamine Oxalate (the purity of this material was determined to be 87% by HPLC).

What is claimed is:

1. A process for producing a reduced amine comprising the steps of:
   (a) protecting a 1,2- or a 1,3-aminoalcohol with trimethylsilyl chloride; and
   (b) reductively coupling the trimethylsilyl protected 1,2- or 1,3 aminoalcohol with an aldehyde to form a reduced amine.

2. A process of claim 1 wherein the alcohol is norepinephrine.

3. A process of claim 1 wherein the alcohol is reacted with trimethylsilyl chloride and a base.

4. A process of claim 3 wherein the base is triethylamine or pyridine.

5. A process of claim 4 wherein one equivalent of norepinephrine is reacted with at least four equivalents of trimethylsilyl chloride and at least four equivalents of base.

6. A process of claim 3 wherein the alcohol is reacted with trimethylsilyl chloride and a base in a suitable solvent.

7. A process of claim 6 wherein the solvent is ethyl acetate or methylene chloride.

8. A process of preparing benzyl arbutamine oxalate comprising the steps of:
   (a) reacting norepinephrine with trimethylsilyl chloride to form a trimethylsilyl-protected norepinephrine;
   (b) reductively aminating the trimethylsilyl-protected norepinephrine with 4-(4-benzyloxyphenyl)-butanal to form trimethylsilyl-protected benzyl arbutamine; and
   (c) removing the trimethylsilyl protecting groups to form the oxalate.

9. A compound of the formula:

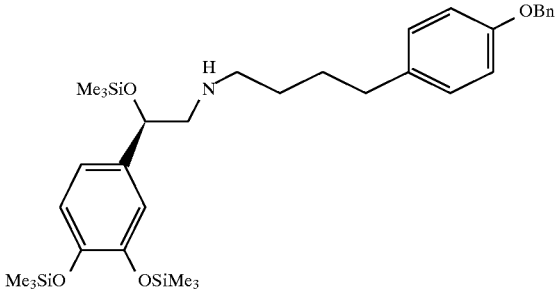

* * * * *

UNITED STATES PATENT AND TRADEMARK OFFICE
CERTIFICATE OF CORRECTION

PATENT NO.    : 5,874,601
DATED         : February 23, 1999
INVENTOR(S)   : Monte et al.

It is certified that error appears in the above-identified patent and that said Letters Patent is hereby corrected as shown below:

Title page,
Line 22, change "Filed: Apr. 5, 1996" to -- Filed: Mar. 14, 1996 --.

Signed and Sealed this

Sixth Day of November, 2001

Attest:

*Nicholas P. Godici*

NICHOLAS P. GODICI
*Attesting Officer*       *Acting Director of the United States Patent and Trademark Office*